United States Patent
Neculaes et al.

(10) Patent No.: US 10,633,645 B2
(45) Date of Patent: Apr. 28, 2020

(54) CALCIUM CONTROLLED ACTIVATION OF PLATELETS VIA ELECTRICAL STIMULATION

(71) Applicant: GENERAL ELECTRIC COMPANY, Schenectady, NY (US)

(72) Inventors: Vasile Bogdan Neculaes, Niskayuna, NY (US); Andrew Soliz Torres, Niskayuna, NY (US); Steve Lambert Klopman, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/984,988

(22) Filed: Dec. 30, 2015

(65) Prior Publication Data

US 2017/0191052 A1 Jul. 6, 2017

(51) Int. Cl.

| | | |
|---|---|---|
| *C12N 13/00* | (2006.01) | |
| *C12N 5/078* | (2010.01) | |
| *A61K 35/19* | (2015.01) | |
| *A61K 33/06* | (2006.01) | |
| *A61K 38/18* | (2006.01) | |
| *A61K 41/00* | (2020.01) | |

(52) U.S. Cl.
CPC .............. *C12N 13/00* (2013.01); *A61K 35/19* (2013.01); *A61K 38/18* (2013.01); *A61K 41/00* (2013.01); *C12N 5/0644* (2013.01); *A61K 33/06* (2013.01)

(58) Field of Classification Search
None
See application file for complete search history.

(56) References Cited

U.S. PATENT DOCUMENTS

| | | | |
|---|---|---|---|
| 5,293,772 A * | 3/1994 | Carr, Jr. ............. | G01N 33/4905 422/73 |
| 5,401,663 A * | 3/1995 | Yonemura ............... | G01N 33/86 252/408.1 |
| 6,322,785 B1 | 11/2001 | Landesberg et al. | |
| 6,326,711 B1 | 12/2001 | Schoenbach et al. | |
| 7,565,201 B2 | 7/2009 | Blackmore et al. | |
| 8,663,146 B2 | 3/2014 | Higgins et al. | |
| 2007/0235329 A1* | 10/2007 | Harding ............. | G01N 33/4905 204/403.01 |
| 2010/0112081 A1 | 5/2010 | Mishra et al. | |
| 2013/0110220 A1 | 5/2013 | Brown | |
| 2014/0106430 A1 | 4/2014 | Hargrave et al. | |
| 2014/0363412 A1 | 12/2014 | Neculaes et al. | |
| 2014/0363881 A1 | 12/2014 | Caiafa | |
| 2015/0202264 A1 | 7/2015 | Neculaes et al. | |
| 2015/0203836 A1 | 7/2015 | Caiafa et al. | |

FOREIGN PATENT DOCUMENTS

| | | |
|---|---|---|
| WO | 2015108778 A1 | 7/2015 |
| WO | 2015/123778 A1 | 8/2015 |
| WO | 2015168015 A1 | 11/2015 |

OTHER PUBLICATIONS

James, M.F.M. 2004. Dose-response relationship between plasma ionized calcium concentration and thrombelastography. Journal of Cardiothoracic and Vascular Anesthesia 18(5): 581-586. specif. pp. 581, 582, 583, 584, 585, 586.*
Scarlett, S.S. 2009. Regulation of intracellular calcium concentration by nanosecond pulsed electric fields. Biochimica et Biophysica Acta 1788: 1168-1175. specif. pp. 1168, 1169, 1170, 1174.*
Gessmann, J. et al. 2013. Plasma clots gelled by different amounts of calcium for stem cell delivery. Langenbeck's Archives of Surgery 398: 161-167. specif. pp. 161, 162, 165, 166.*
Thakur, M. et al. 2012. A review of thromboelastography. International Journal of Perioperative Ultrasound and Applied Technologies 1(1): 25-29. specif. pp. 25, 26.*
U.S. Appl. No. 14/674,971, filed Mar. 31, 2015, Neculaes.
Zhang et al., "Nanosecond Pulse Electric Field (nanopulse): A Novel Non-ligand Agonist for Platelet Activation", Archives of Biochemistry and Biophysics, vol. No. 471, Issue 2, pp. 240-248, Mar. 15, 2008.
Torres et al., "Platelet Activation Using Electric Pulse Stimulation: Growth Factor Profile and Clinical Implications", Journal of Trauma and Acute Care Surgery, vol. No. 77, Issue No. 3, pp. S-94-S-100, Sep. 2014.
PCT Search Report and Written Opinion issued in connection with corresponding PCT Application No. PCT/US2016/69197 dated Mar. 30, 2017.
Zhang et al., "Nanosecond pulse electric field (nanopulse): A novel non-ligand agonist for platelet activation", Archives of Biochemistry and Biophysics, vol. 471, Issue 2, pp. 240-248, Mar. 15, 2008.
Freitag, Julian et al.; "Photoactivated platelet-rich plasma therapy for a traumatic knee chondral lesion", BMJ Case Reports 2012: doi 10.1136/bcr-2012-006858 (abstract only).
Torres et al., "Platelet activation using electric pulse stimulation: Growth factor profile and clinical implications", Journal of Trauma and Acute Care Surgery, 77(3 Suppl 2):S94-S100, Sep. 2014.
AdiStem PhotoActivated PRP & Stem Cell Technology website downloaded 2014: http://www.adistem.com/technology/prp/.

(Continued)

*Primary Examiner* — Renee Claytor
*Assistant Examiner* — Sharon M. Papciak
(74) *Attorney, Agent, or Firm* — Fletcher Yoder, P.C.

(57) ABSTRACT

The present disclosure relates to the generation of an activated platelet product in which one or more of the presence or absence of clots, the timing of clot formation (if present), and/or the mechanical strength of clots (if present) is controlled by the presence or concentration of calcium ions during the activation process. In certain embodiments, the calcium ion concentration is controlled in the presence of pulsed electric fields or a chemical activator (e.g., thrombin) as part of the activation process.

18 Claims, 5 Drawing Sheets

(56) References Cited

OTHER PUBLICATIONS

Xiao, S., et al., "Pulsed Power for Wound Healing," IEEE International Conference on Power Modulators and High Voltage, pp. 69-72 (May 27-31, 2008).

International Search Report and Written Opinion issued in connection with corresponding PCT Application No. PCT/US2016/69197 dated Jul. 3, 2017.

\* cited by examiner

CALCIUM CONTROLLED ACTIVATION OF PLATELETS VIA ELECTRICAL STIMULATION

BACKGROUND

The subject matter disclosed herein relates generally to platelet therapy used in various medical applications, such as treatments for surgery or trauma. Certain embodiments relate to platelet activation and control of clotting by varying various activation conditions including, but not limited to, presence and characteristics of a pulsed electric field and calcium presence and concentration.

Use of platelet gel (also called "activated platelet rich plasma") is an emerging therapeutic approach that may be employed in clinic or other health care facility for a variety of applications, including promoting wound healing (such as after surgery) and hemostasis. In particular, interest in the use of platelet therapy as a wound healing treatment exists for many types of injuries and conditions, such as nerve injuries, tendinitis, osteoarthritis, cardiac muscle injury, and bone repair and regeneration. In addition, the derivation of the platelet gel used on a patient may be autologous, meaning that the platelets are derived from the patient's own tissues and/or fluids. Thus a blood sample, from the patient may be used to derive the platelet gel used to treat the patient.

By way of example, a doctor may draw blood from a patient. The blood may then be centrifuged to generate platelet rich plasma (PRP). Upon platelet activation, the platelets within the blood release growth factor and proteins that facilitate and promote the wound healing cascade. The clinical workflow may, therefore, involve drawing blood from the patient, centrifuging the blood to separate out the platelets, and performing an ex vivo platelet activation, such as using bovine thrombin. The activated platelets or platelet gel may then be applied to the wound or other treatment region. In instances where in vivo platelet activation is instead employed, the doctor may apply the PRP to the site without adding a platelet activator. Platelet activation, which includes growth factor release and clotting, is usually induced by the collagen within connective tissue.

For such ex vivo applications, where thrombin (e.g. bovine thrombin) is used to induce platelet activation, the resulting growth factor levels may be fixed based on the biologic response. That is the amounts and/or respective ratios or proportions of different growth factors are dictated by the nature of the thrombin-based activation. In such reactions, therefore, the clinician is unable to adjust or manipulate the respective amounts or proportions of different growth factors, and must instead make do with the conventional activation compositions. Further, in certain clinical scenarios, it may be desirable to have or not have clotting and/or, in the presence of clotting, to control for the mechanical strength or other characteristics of the clot.

BRIEF DESCRIPTION

In one embodiment, a method for generating an activated product is provided. In accordance with this method, a platelet-rich plasma (PRP) sample is prepared for activation. The PRP sample is prepared by adding calcium ions at a respective concentration. The respective concentration is selected based upon whether clots are to be present in an activated product composition generated using the PRP sample and, if clotting is to be present, one or more of a time until clot formation or a mechanical strength of the clots. The PRP sample is positioned with respect to electrodes of an electromagnetic stimulation apparatus. A set of electrical pulse parameters is specified. The PRP sample is exposed to one or more electrical pulses generated in accordance with the parameter values. The PRP sample, when exposed to the one or more electrical pulses, yields an activated product composition comprising one or more growth factors and having the specified clotting characteristics.

In a further embodiment, a method for generating an activated product is provided. In accordance with this method, an anticoagulant-treated platelet-rich plasma (PRP) sample is prepared for activation. Calcium ions are added to the PRP sample to achieve a calcium ion concentration selected from a range of possible concentrations. The concentration is selected based upon target levels of one or more growth factors to be present in an activated product composition generated using the PRP sample. The PRP sample is exposed to electrical activation stimulus. The PRP sample, when exposed to the electrical activation stimulus, yields an activated product composition comprising the one or more growth factors at the target levels. Varying the calcium ion concentration without varying the electrical activation stimulus changes one or both of the absolute or relative levels of the one or more growth factors.

In an additional embodiment, a method for controlling clot mechanical strength in a platelet gel is provided. In accordance with this method, a prospective mechanical strength of one or more clots to be generated in the platelet gel is determined. The prospective mechanical strength is greater than what would be observed by generating the platelet gel using thrombin alone. Based on the prospective mechanical strength, a calcium ion concentration corresponding to the prospective mechanical strength is selected from among a plurality of calcium ion concentrations. The platelet gel is generated by activating a platelet-rich plasma (PRP) sample comprising calcium ions at the selected calcium ion concentration. The PRP sample is activated using electrical stimulus. The platelet gel comprises clots that, once formed, have the prospective mechanical strength.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
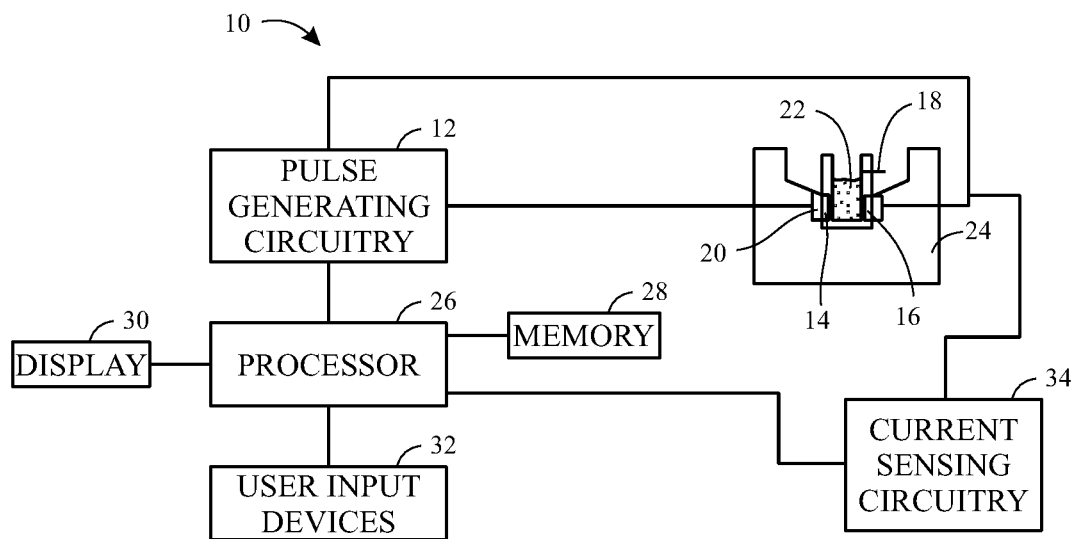
FIG. 1 is a schematic of a pulse generation system, in accordance with aspects of the present disclosure.

One or more specific embodiments of the present subject matter will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The techniques presented herein are referenced and applied to material objects and concrete examples of a practical nature that demonstrably improve the present technical field and, as such, are not abstract or purely theoretical.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Platelet activation and/or aggregation may be used to treat wounds in vivo and/or ex vivo. For in vivo platelet activation, unactivated platelet rich plasma (PRP) is applied or injected at the site of injury and activated by naturally occurring compounds within the body, such as collagen present in the connective tissue.

During conventional ex vivo processes, platelets in drawn and separated blood are exposed to a platelet activating compound, such as thrombin, which induces the release of growth factors (e.g., platelet-derived growth factor (PDGF)). For example, for ex vivo platelet activation, a doctor may draw blood from a patient and centrifuge the blood sample to produce a platelet rich plasma (PRP) sample. A source of calcium ions and a platelet activating compound, such as thrombin, may be added to the PRP sample to trigger platelet activation and to form a gel containing the growth factors that is then applied to the wound.

Approaches discussed herein relate to ex vivo platelet (or other cell) activation and growth factor release in the presence of different concentrations of calcium ions ($Ca^{++}$), which may be introduced to the activation mixture in the form of a salt (e.g., $CaCl_2$) (such as $CaCl_2$ provided in the concentration range of 2.5 mM to 20 mM, including, but not limited to: 2.5 mM 5.0 mM, 7.5 mM, 10 mM, 15 mM, 20 mM, and 25 mM). The calcium added should not be confused with the final concentration of calcium in the sample. It should also be appreciated that in certain implementations, the PRP sample to which the calcium is added may include a known amount of an anticoagulant (e.g., ACD-A), which may factor into the determination of the amount of calcium added. In addition, the activation mixture may be exposed to one or more customizable energy exposure protocols (e.g., one or more electrical pulses). The presence of different concentrations of calcium ions, with or without the energy exposure, may, in accordance with certain implementations discussed herein, be used to control or alter clot formation arising from the platelet activation process and, in some implementations, may prevent clotting altogether. Such control over clot formation may be useful in contexts where the activated platelet product will be applied topically (where clotting may be desirable) versus applications where the product may be injected (where clots would be unsuitable. In addition, varying the mechanical strength of clots may be achieved by controlling one or both of the calcium ion concentration in the activation mixture or energy exposure (e.g., electrical) parameters, as discussed herein. By way of example, by the addition of calcium ions in the activation process, as discussed herein, the resulting mechanical strength of the clots formed in the activated platelet product is greater than what would be seen in a thrombin-based activation alone (i.e., without the addition of the calcium ions). Lastly, manipulation of one or both of the calcium ion concentration in the activation mixture or energy exposure (e.g., electrical) parameters, as discussed herein, may be used to control, customize, or optimize the release or relative proportions of one or more growth factors in the resulting activated platelet product.

Thus, by way of example, ex vivo platelet activation as discussed herein may involve exposing a blood sample, such as a PRP sample, or any suspension containing platelets (e.g., a platelet suspension or whole blood), to electrical pulses (e.g., exposure to pulsed electric fields) or other suitable activating energy in the presence of $Ca^{++}$ ions to trigger platelet activation. In certain implementations electrical stimulation or activation may be applied using different electrical parameters (e.g. amplitude, voltage, electric field, energy density, current, pulse width, number of pulses, and so forth), with different parameters or combinations of parameters in conjunction with a specified concentration of $Ca^{++}$ to achieve different growth factor levels and/or to control aspects of clot formation. As a result, an activated composition having specific growth factor and clotting characteristics may be generated and, conversely, the generation of an activated composition having particular growth factor and/or clotting characteristics may determine the electrical pulse parameters and $Ca^{++}$ concentration employed in activating a given cellular composition.

As discussed above, control of the $Ca^{++}$ concentration in the activation mixture is the basis for various implementations discussed herein. Certain of these implementations may also utilize pulsed electric fields as part of the activation protocol. With this in mind, FIG. 1 shows schematically a pulse generation system 10 for ex vivo platelet activation using $Ca^{++}$ concentrations suitable for generating a composition having a particular growth factor profile and clotting characteristics. The system 10 includes pulse generating circuitry 12 and opposing electrodes (or arrays of electrodes) 14 and 16. In the depicted example, the electrodes 14 and 16 are spaced apart on opposing sides of a cuvette 18. That is, the cuvette 18 is disposed between the electrodes and the electrodes 14 and 16 are coupled to the pulse generating circuitry via contacts 20. That is, conductive coupling (i.e., contact coupling) is demonstrated in the depicted example. It should be understood, however, that this contact-coupling example is provided only to facilitate explanation and to provide a useful context for explaining the present approach, and is not the only suitable mechanism for exposing a sample (as discussed herein) to activation energy. For example, in other implementations, non-contact coupling techniques (such as capacitive or inductive coupling techniques) may be employed to accomplish the discussed energy coupling. Thus, as discussed herein, energy coupling to the platelet suspension should be understood as occurring via any suitable mechanism, whether involving contact between the sample container and conduit and electrodes (as shown in this example) or absent such contact using inductive or capacitive effects.

Regardless of the physical or structural implementation, the pulse generating circuitry 12, when in operation, electrically stimulates or activates a blood, blood component or platelet suspension sample 22 in the presence of $Ca^{++}$ within the cuvette 18 so as to activate platelets or other cell types within the sample 22 that release proteins and/or growth factors when activated or stimulated. As discussed herein, this may take the form of applying pulsed electric fields to the sample contained within the cuvette 18 when the pulse generating circuitry 12 is operating, regardless of the manner in which the electrodes 14 and 16 and cuvette 18 are physically integrated or interfaced. The system 10 may be configured to accept or hold different sizes of cuvettes, such as cuvettes of different diameter or width.

The cuvette 18 may be disposable and/or removable from a sample holder 24 that incorporates the electrodes 14 and 16. Insertion of the cuvette 18 into the sample holder 24 and contact of the electrodes 14 and 16 with the contacts 20 allows the pulse generating circuitry 12 to produce electrical pulses that span the sample 22. As will be appreciated, the cuvette 18 is merely one example of a suitable sample container, and other types of vessels configured to hold the sample 22, contact the electrodes 14 and 16, and conduct the electrical pulses may be used in conjunction with the system 10. As discussed herein, the spacing between the electrodes 14 and 16 may influence the strength of the pulse's electric field, which is defined as the ratio of the applied voltage and the cuvette gap distance. For example, exposing a 1 cm wide cuvette to a 1 kV pulse yields a field strength of 1 kV/cm. Field strength, electrode separation distance, and other parameters related to the generated electrical pulses are factors, as discussed herein, that may be varied or adjusted to vary the growth factor levels with respect to one another during an activation procedure.

As may be appreciated, the depicted cuvette or container based activation system is suitable for a batch-type processing environment. However, a flow-through type processing environment may instead be employed, where a conduit instead passes through the electrodes 14 and 16, which may be on opposite sides of the conduit or surrounding the conduit. Such a flow through arrangement allows a sample to be continuously flowed through the conduit to be exposed to the pulsed electrical fields for activation, with the activated product being collected in a continuous or semi-continuous manner. In addition to, or instead of, the electrical parameters at the electrodes and/or the width between the electrodes 14 and 16, other parameters may also be adjusted so as to configure the activation process. For example, the flow rate of the sample (e.g., a platelet suspension) through the conduit and/or the diameter of the conduit may also be accounted for or adjusted as a factor or parameter of the activation process. That is, in addition to the electrical parameters specified for the electrodes, one or both of the flow rate and the electrode spacing may determine the electrical field exposure (or field density exposure) experienced by the sample during activation.

The system may include control and input circuitry and may be implemented in a dedicated housing or may be coupled to a computer or other processor-based control system. For example, the system 10 may include or communicate with a processor 26 that controls the pulse generating circuitry 12. Additional components of the system 10 may include a memory 28 storing instructions that are executed by the processor 26. Such instructions may include protocols and/or parameters for generating the electrical pulses using the pulse generating circuitry 12. The processor 26 may include, for example, general-purpose single- or multi-chip microprocessors. In addition, the processor 26 may be any conventional special purpose processor, such as an application-specific processor or circuitry. The memory 28 may be any suitable non-transitory computer-readable medium such as a random access memory, mass storage device, a solid state memory device, or removable memory. In addition, a display 30 may provide indications to an operator related to the operation of the system 10. The system 10 may include a user input device 32 (e.g., a keyboard, mouse, touchscreen, trackball, hand held device such as PDA or smart phone or any combination thereof) for activating the pulse generating circuitry 12, selecting or specifying appropriate pulse parameters, or selecting a preconfigured pulse profile from among a number of such profiles (such as profiles each corresponding to different activated product compositions or characteristics (e.g., growth factor profiles, clot strength, presence or absence of clotting, and so forth).

The pulse generation system 10 as discussed herein may be implemented as a single-purpose device for platelet or other cell-type activation or as a multi-purpose device that may be used for other electric field exposure applications, such as electroporation, accelerated cell growth via exposure to electrical stimulation in addition to platelet (or other cell-type) activation. Further, the system 10 may be configured to generate electrical pulses according to one or more defined protocols and/or using one or more parameters that may be varied to generate activated products having different characteristics. With respect to the various electrical pulse factors or parameters, these factors include, but are not limited to: cuvette spacing (i.e., the width of the cuvette 18 across which the pulse is applied), flow rate (in a flow through implementation), voltage, electric field (e.g., strength or density), current, pulse width, pulse duration, and the number of pulses applied.

The protocols may be generated by user input and/or may be stored in the memory 28 to be selected by the user, such as from a list or menu. The pulse generating circuitry 12 may operate under control of the processor 26 to implement protocols that use a specified electric field strength, $Ca^{++}$ concentration, pulse length, total exposure time, flow rate (for a flow-through implementation) or other characteristic so as to generate a customized activated cellular composition. Such a protocol may be determined by empirical or theoretical studies, such as to correspond to a desired clinical use. In other implementations, the system 10 may be configured to receive a user input related to one or more of the electric field strength, $Ca^{++}$ concentration, pulse length, flow rate, and/or total exposure time, i.e., the user can vary or specify one or more of these operational parameters. Further, the system 10 may be configured to generate a particular pulse shape or to generate a series of pulses that may differ from one another according to a user input and/or a stored protocol setting.

By way of example, a pulse generated by the system 10 may have a duration from about 1 nanosecond to about 100 microseconds, and an electric field strength from about 0.1 kV/cm to about 350 kV/cm, depending on the application. As noted above, the electric field strength of the pulse is the applied voltage divided by the distance between the electrodes 14 and 16. While the pulses generated by the system 10 typically have an electric field strength of 0.1 kV/cm or greater, the pulses typically will not exceed the breakdown field of the suspension which includes the cells.

The pulse generation system 10 may also include sensing functionality. That is, the pulse generation system 10 may be configured to expose the sample 22 to a sensing signal, which may be an electrical pulse with an electric field strength below that of the electrical pulses used for cellular activation. The pulse generation system 10 may, as depicted in FIG. 1, include current sensing circuitry 34, which may acquire and/or process the sensing signal to estimate some of the electrical or chemical properties of the sample 22, including, but not limited to conductivity and permittivity. In practice, such sensing circuitry may be used to ascertain a $C1^{++}$ concentration within the sample being processed, such as to confirm that the $Ca^{++}$ concentration conforms to a selected protocol and/or to adjust operational parameters based on the observed or measured $Ca^{++}$ concentration present in the sample.

The current sensing circuitry 34 may be coupled to the processor 26, which may control the generation and processing of the sensing signal and may perform a portion of the processing. In other implementations, the current sensing circuitry 34 may include a dedicated processor to control the processing of the sensing signal and may communicate with the processor 26 to report the results. Alternatively, the current sensing circuitry 34 may be integral with the pulse generating circuitry 12, providing inputs used in the generation of subsequent activation electrical pulses. In still other implementations, the processing of the sensing signal may be performed by a dedicated processor as described above or the processor 26.

Study Design—In one study, combinations of these parameters where tested in conjunction with other control or activation scenarios. In this study, concentrated platelet-rich plasma (PRP) was prepared for the study. Donors were qualified for participation if they were 18 years old or older, were free of aspirin or other antiplatelet medication for 10 days or more, and were free of all other non-steroidal anti-inflammatory drugs for 3 days or more. Following a 2 mL discard, 120 mL of blood was collected from each of 5 volunteer donors into $\frac{1}{10}^{th}$ volume of acid-citrate-dextrose solution A (ACD-A). PRP was prepared according to the manufacturer's recommendation using the Harvest Smart-PreP2 System (Harvest Technologies, Plymouth, Mass., USA) with two 60 mL cartridges. The resultant PRP was pooled prior to further treatment. Complete blood cell counts were performed on the ACD-anticoagulated whole blood and the concentrated PRP in a Sysmex XN Hematology Analyzer.

The prepared PRP was then activated using one of two pulsed electric fields (PEF), i.e., PEF A or PEF B, or in the presence of bovine thrombin (1 U/mL final concentration, Biopharm Laboratories LLC, Bluffdale, Utah, USA). Prior to activation with PEF or thrombin, PRP samples were recalcified by addition of $\frac{1}{100}^{th}$ volume of $CaCl_2$ (2.5 mM or 20 mM final concentrations, Bachem, Torrance, Calif., USA). A total of 2 mL of concentrated PRP was treated under each condition in a 2 mm electroporation cuvette (Molecular BioProducts, San Diego, Calif., USA) in a system corresponding to that described with respect to FIG. 1. PEF A was parameterized as follows: one pulse; pulse widths were approximately 5 microseconds, ~3.3 kV voltage amplitude, and more than 300 A current. PEF B was parameterized as follows: 120 bipolar pulses, 1 pulse per second, ~800 V (voltage) and ~70 A (current). Controls included PRP treated with buffer alone (saline) with high $CaCl_2$ (i.e., 20 mM levels of added $CaCl_2$) alone, and thrombin with low (2.5 mM) and high (20 mM) added $CaCl_2$.

Table 1 summarizes the various combinations of study parameters.

TABLE 1

|  | Run 1 | Run 2 | Run 3 | Run 4 | Run 5 | Run 6 | Run 7 | Run 8 |
| --- | --- | --- | --- | --- | --- | --- | --- | --- |
| PEF | A | B | A | B |  |  |  |  |
| $CaCl_2$ | 2.5 mM | 2.5 mM | 20 mM | 20 mM | 2.5 mM | 20 mM |  | 20 mM |
| Bovine Thrombin |  |  |  |  | 1 U/mL | 1 U/mL |  |  |
| Buffered Saline |  |  |  |  |  |  | 10 mM | 10 mM |
| NaCl |  |  |  |  |  |  | 0.15M | 0.15M |

Endpoints measured included: (1) clot formation kinetics and strength by thromboelastography (TEG) and prothrombin fragment F1.2 generation, (2) platelet surface expression of alpha granule (P-selectin) and T-granule (toll-like receptor 9 (TLR9), protein disulfide isomerase (PDI)) markers measured by flow cytometry, (3) factors released from platelets into the supernatant (EGF, PDGF, VEGF, PF4, PDI). All endpoints except TEG were measured in samples taken 15 min after activation.

Thromboelastography and Activation of Plasma Prothrombin—For analysis of clot formation in the activated product (i.e., platelet gel), 360 µL of activated PRP was transferred to the TEG cup and recordings initiated immediately following exposure of PRP to activating conditions. Measurements were obtained using a TEG 5000 Hemostasis Analyzer System (Haemonetics Corporation, Braintree, Mass., USA). Clotting kinetics and characteristics were followed for 30 minutes.

To determine the degree to which the calcium, PEF, thrombin, and control conditions contributed to the conversion of plasma prothrombin to active thrombin, samples were centrifuged, the supernatant recovered, and F1.2 was measured by ELISA (Enzygnost, Siemens, Marburg, Germany) according to the distributor's manual in supernatants collected 15 min after PRP activation.

Platelet Alpha Granule and T-granule Release—Following activation of PRP, a portion of each sample was mixed with the peptide Gly-Pro-Arg-Pro (GPRP) which prevents fibrin polymerization into clots, thereby allowing flow cytometric analysis of platelet surface markers by flow cytometry. In particular, flow cytometry was used to assess differential release of platelet granules and granule contents as measured by changes in platelet surface P-selectin (CD62P) (for alpha granules) and platelet surface PDI and TLR9 (for T-granules). Samples for flow cytometry were fixed fifteen minutes after activation by addition of an equal volume of 2% formaldehyde in 10 mM HEPES, 0.15 M NaCl, pH7.4.

Samples were diluted 12-fold in HEPES-Saline buffer (10 mM HEPES, 0.15 M NaCl, pH 7.4; chemicals from Sigma, St. Louis, Mo., USA) then added to a mixture of FITC-conjugated anti-TLR9 (clone 5G5, Abcam, Cambridge, Mass., USA), phycoerythrin (PE)-conjugated P-selectin (clone AK4, BD Pharmingen, San Diego, Calif., USA) and CD41-PerCP-Cy5.5 (clone HIP8, BD Pharmingen, San Diego, Calif., USA) or to a mixture of FITC-conjugated anti-P-selectin (clone AK4, BD Pharmingen, San Diego, Calif., USA), PE-conjugated PDI (clone 1D3, Abcam, Cambridge, Mass., USA) and CD41-PerCP-Cy5.5. Non-specific staining was determined in parallel using a sample reacted with a mixture of isotype-matched FITC, isotype-matched PE and PerCP-Cy5.5-conjugated normal Ig. After 30 minutes of staining at room temperature, 400 µL of 1% formaldehyde in HEPES-Saline buffer was added. Flow cytometric analysis was performed in a calibrated Becton Dickinson FACSCalibur.

T-granule release was further evaluated by measurement of PDI by ELISA (Cloud-Clone Corp., Houston, Tex., USA) according to the distributor's manual in supernatants collected 15 min after PRP activation.

Differential Release of Platelet Granules and Growth Factors—Levels of epidermal growth factor (EGF), platelet-derived growth factor (PDGF), vascular endothelial growth factor (VEGF), and platelet factor 4 (PF4) in the supernatants of the treated PRP were measured using commercially available ELISA kits (EGF and PDGF R&D Systems, Minneapolis, Minn., USA; VEGF, Eagle Biosciences, Nashua, N.H., USA; PF4, Abcam, Cambridge, UK).

Analysis—Observed data were analyzed using GraphPad Prism version 5.0a (GraphPad Software, La Jolla, Calif., USA). Normally distributed data (as judged by the D'Agostino and Pearson omnibus normality test) are summarized as mean±standard deviation or mean±standard error of the mean, as indicated. Non-parametric data are reported as median and interquartile range or median and range. One way ANOVA was used for comparison of three or more groups, with Tukey's multiple comparison post-test for individual comparisons.

Figure 2:
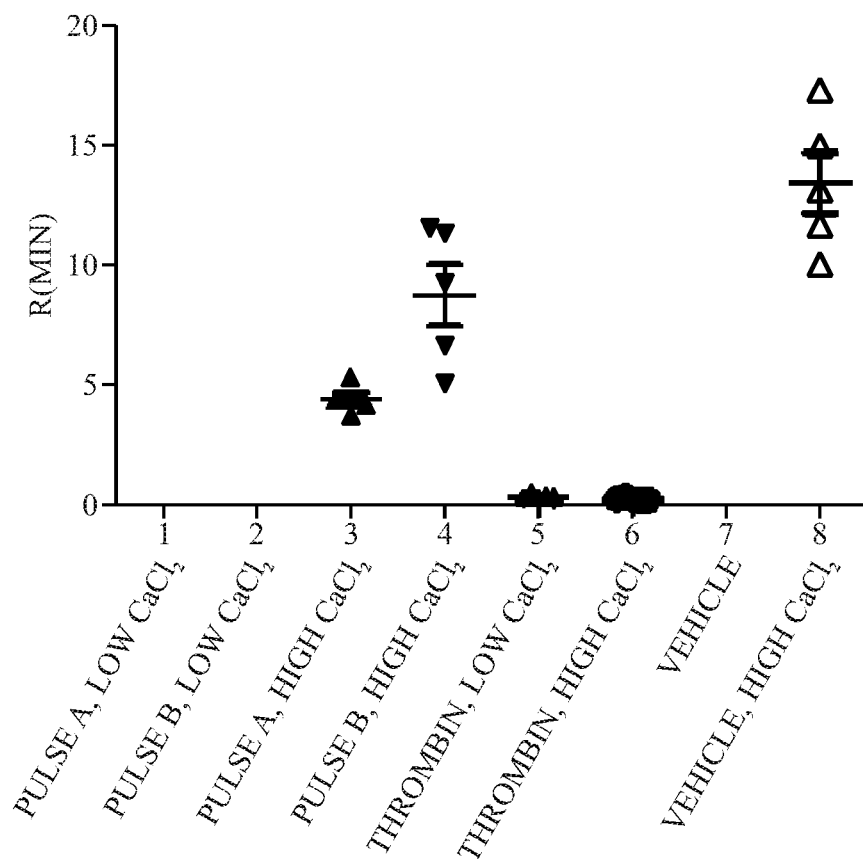
FIG. 2 graphically depicts time to initial clot formation (clotting time) for a set of study results, in accordance with aspects of the present disclosure.
Figure 3:
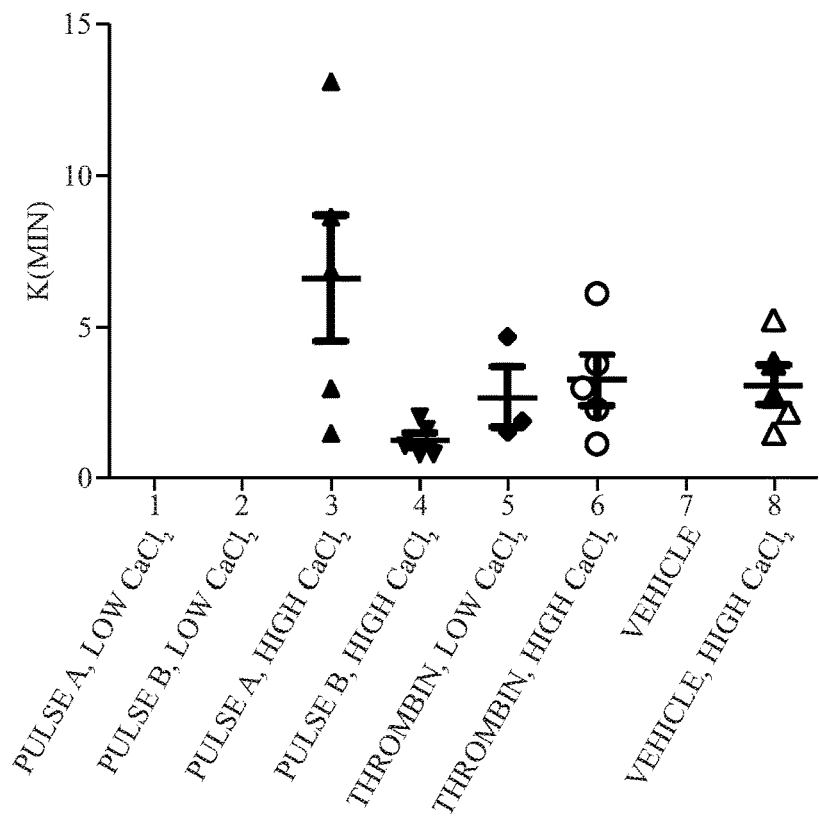
FIG. 3 graphically depicts clot kinetics for a set of study results, in accordance with aspects of the present disclosure.
Figure 4:
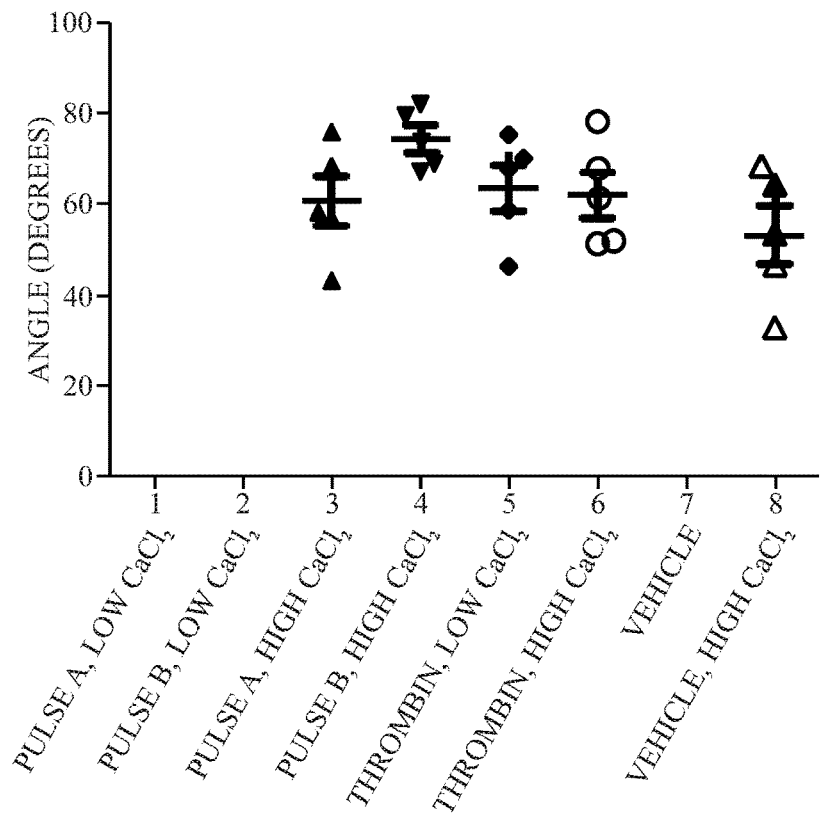
FIG. 4 graphically depicts fibrinogen level for a set of study results, in accordance with aspects of the present disclosure.
Figure 5:
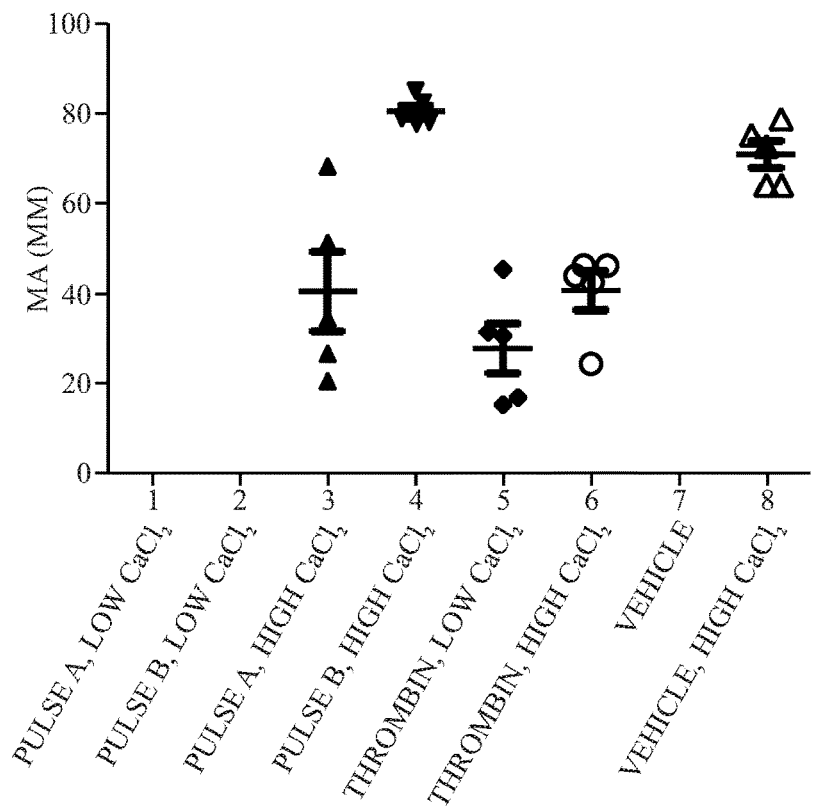
FIG. 5 graphically depicts clot strength for a set of study results, in accordance with aspects of the present disclosure.

Results—Clot Kinetics and Strength (TEG and Thrombin Generation)—A comparison of pulse electric field (PEF) conditions and calcium levels vs. bovine thrombin on clotting kinetics and clot strength as measured by thromboelastograph is shown in Table 2.

required to reach a pre-defined level of clot strength and represents clot kinetics (graphically depicted in FIG. 3). TEG Angle is the slope in degrees for the change in amplitude over time due to the rapidity of fibrin build-up and cross-linking and represents fibrinogen level (graphically depicted in FIG. 4). TEG maximum amplitude (MA) (graphically depicted in FIG. 5) is the maximum amplitude in millimeters and is a direct function of the maximum dynamic properties of fibrin and platelet bonding and the ultimate strength of fibrin clot. TEG MA is considered to represent platelet function and/or aggregation. In each of FIGS. 2-4, individual results are plotted, along with the mean and standard error of the mean (SEM)

As shown in Table 2 (and graphically depicted in FIG. 2), time to initial clot formation was shortest for thrombin treated samples (runs 5 and 6), occurring in less than a minute, conversely, run 3 (PEF A, 20 mM $CaCl_2$) initiated clotting at approximately four 4 minutes, run 4 (PEF B, 20 mM $CaCl_2$) initiated clotting at approximately 9 minutes, and high calcium alone (run 8) initiated clots at about thirteen minutes. Clots were not detected by TEG up to 30 min after activation in run 1 (PEF A, 2.5 mM $CaCl_2$), run 2 (PEF B, 2.5 mM $CaCl_2$), or run 7 (i.e., treatment with buffer (no calcium)), which are not shown in Table 2.

These results were consistent with the thrombin generation results, in which the highest levels of F1.2 were observed for PRP incubated with high calcium alone (run 8), while F1.2 was undetectable for the no calcium control (run 7) and for both runs 1 and 2 (PEF A, 2.5 mM $CaCl_2$ and PEF B, 2.5 mM $CaCl_2$). This was consistent with the results of the TEG studies, which showed no detectable clotting in the absence of calcium (run 7) or after 30 minutes treatment with PEF A, 2.5 mM $CaCl_2$ and PEF B, 2.5 mM $CaCl_2$ (runs 1 and 2).

Thus, as shown in these results, neither pulsed electric field tested yielded an activated product that clotted in the low $Ca^{++}$ (2.5 mM $CaCl_2$) scenario. In other scenarios, the clotting time varied based on the activation approach, with PEF A and high $Ca^{++}$ (20 mM $CaCl_2$) clotting in ~4 minutes, PEF B and high $Ca^{++}$ clotting in ~8 minutes, and thrombin in the presence of high or low $Ca^{++}$ clotting in ~1 minute. As may be appreciated, the significance of this is that $Ca^{++}$ levels, in conjunction with activation approach, may be used to control whether clotting occurs at all and, if clotting does occur, the time to initial clot formation (e.g., time to clotting).

TABLE 2

|  | Run 3 PEF A/20 mM $CaCl_2$ | Run 4 PEF B/20 mM $CaCl_2$ | Run 5 Thrombin/ 2.5 mM $CaCL_2$ | Run 6 Thrombin/ 20 mM $CaCL_2$ | Run 8 Buffered Saline/20 mM $CaCl_2$ |
|---|---|---|---|---|---|
| TEG R (min) | 4.4 ± 0.6* | 8.7 ± 2.9* | 0.3 ± 0.1 | 0.2 ± 0 | 13.4 ± 2.8* |
| TEG K (min) | 6.6 ± 4.6 | 1.3 ± 0.5 | 2.7 ± 1.7 | 3.3 ± 1.9 | 3.1 ± 1.5 |
| TEG Angle (°) | 60.6 ± 12.2 | 74.2 ± 6.4 | 63.4 ± 11.3 | 61.9 ± 11.2 | 53.2 ± 14 |
| TEG MA (mm) | 40.6 ± 19.5 | 80.7 ± 3* | 28.1 ± 12.4 | 40.9 ± 9.3 | 71.1 ± 6.6* |

Figure 6:
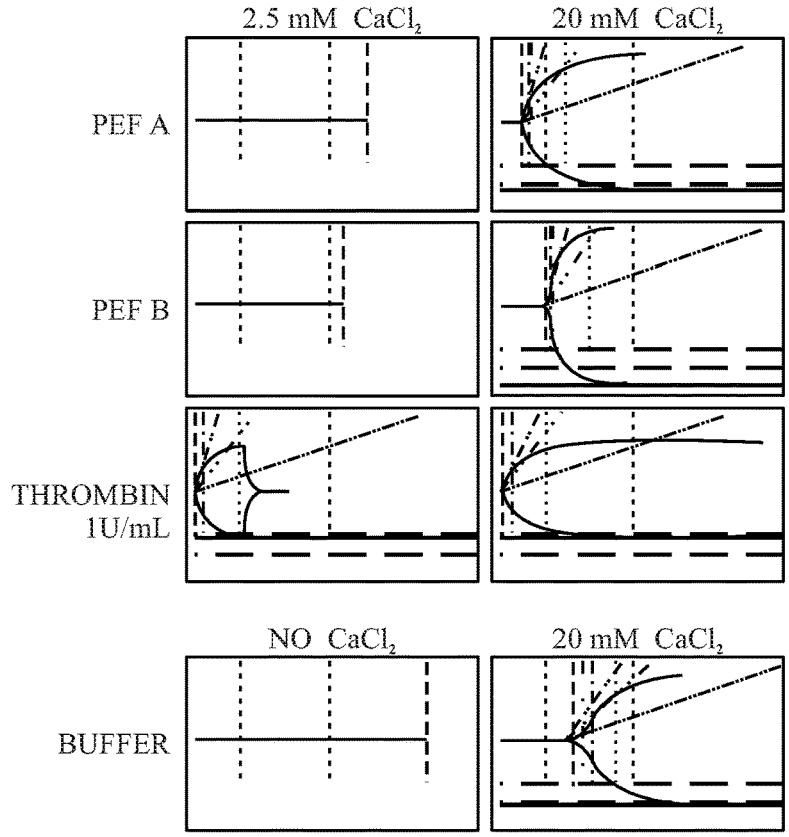
FIG. 6 depicts representative TEG tracings depicting clot mechanical strength (MA) observed over time for one study participant, in accordance with aspects of the present disclosure.

*$p < 0.05$ vs. Thrombin, 20 mM $CaCl_2$;

With respect to the TEG results, time to initial clot formation, R, for the respective study factors is graphically depicted in FIG. 2. Specifically TEG R represents the enzymatic portion of coagulation and is the period of latency (in minutes) from time that blood was placed in TEG analyzer until the initial fibrin formation. TEG K is the time Despite taking more time for initial clot formation to occur, clot strength (MA) (shown in FIG. 5) was highest in run 4 (PEF B, 20 mM $CaCl_2$) and the calcium alone control (run 8). Clot strength (MA) was similar for run 6 (thrombin, 20 mM $CaCl_2$) and run 3 (PEF A, 20 mM $CaCl_2$) although clot strength appears to be more variable with run 3. In general, addition of calcium ions in the activation process yielded a product with clots having a mechanical strength greater than what is seen in activation processes using thrombin alone, without added calcium. By way of further example, FIG. 6 depicts representative TEG tracings depicting the clot mechanical strength (MA) observed over time for one of the volunteers.

With respect to these results and in summary, re-calcification of ACD-anticoagulated PRP with 20 mM $CaCl_2$ results in an estimated free $Ca^{++}$ concentration of 5 mM (calculated based on the overall binding constant between citrate and calcium ions) and results in thrombin generation as evidenced by F1.2 production and the formation of a clot whose strength (elastic modulus, derived from TEG maximum amplitude) was greater than that of clots formed following direct addition of thrombin. Adding PEF A or PEF B treatment immediately after re-calcification of PRP with 20 mM $CaCl_2$ shortened the time required to initiate clotting and still yielded clots that were as strong (PEF A, 20 mM $CaCl_2$) or stronger (PEF B, 20 mM $CaCl_2$) than those produced by thrombin, 20 mM $CaCl_2$. Thus, the strength of platelet gels formed with 20 mM $CaCl_2$ and PEF A and PEF B permits manipulation of the material and placement in position on a wound. Clots failed to form when PRP supplemented with 2.5 mM $CaCl_2$ (estimated 90 μM free $Ca^{++}$) was stimulated with PEF A or PEF B, making these conditions unsuitable for preparation of platelet gels for wound healing but allowing easy separation of released factors.

With respect to the thrombin generation aspect of these results, the current results of higher levels of F1.2 in the presence of high calcium alone compared to thrombin with low or high calcium suggest that addition of calcium without thrombin favors the generation of Factor Xa (which is involved in the activation of thrombin from prothrombin), likely via the tissue factor pathway. PEF A and PEF B in the presence of high calcium produce F1.2 levels higher than that produced by direct addition of bovine thrombin but lower than that produced by high calcium alone, suggesting that calcium mediated Factor Xa production is less efficient in the presence of PEF A and B but greater than that produced in the presence of low or high calcium and thrombin.

Differential Exposure of Platelet Alpha Granule and T Granule Markers—Results for this portion of the study are shown in Tables 3 and 4.

In the platelet alpha granule and T granule marker portion of the study, as shown in Table 3, greater than 80% of platelets were positive for P-selectin, a platelet alpha granule membrane protein in runs 5 and 6 (thrombin with 2.5 mM or 20 mM $CaCl_2$) as well as in runs 1 and 3 (i.e., PEF A, 2.5 mM or PEF A, 20 mM $CaCl_2$), while a lower percentage (53.5±33, mean±SD) of platelets were P-selectin positive in run 4 (PEF B, 20 mM $CaCl_2$). High calcium alone (run 8) caused a modest increase in the percent P-selectin positive platelets compared to run 2 (PEF B, 2.5 mM $CaCl_2$) and the no calcium control (run 7). The mean fluorescence intensity (MFI) of P-selectin per particle with PEF treatment was lower than that seen with thrombin and low or high $CaCl_2$.

Platelet surface toll-like receptor 9 (TLR9) was highest in run 5 (thrombin, 2.5 mM $CaCl_2$). Lower TLR9 and highly variable levels of TLR9 were observed for run 4 (PEF B, 20 mM $CaCl_2$), and negligible TLR9 expression was observed for runs 1 and 3 (PEF A, 2.5 mM $CaCl_2$ and PEF A, 20 mM $CaCl_2$), run 2 (PEF B, 2.5 mM $CaCl_2$), and for the no calcium and high calcium only controls (runs 7 and 8). Overall, while the levels of TLR9 were lower than P-selectin, the pattern of TLR9 expression was not distinctly different from that seen for P-selectin. In contrast, the pattern of PDI expression was unique in that the highest levels were seen in run 6 (thrombin, 20 mM $CaCl_2$) instead of run 5 (thrombin, 2.5 mM $CaCl_2$).

Turning to Table 4, T granule release was also estimated by release of PDI into the supernatants of treated PRP samples as measured by ELISA. PDI levels were greatest in the supernatants of run 1, with PRP activated with PEF A and 2.5 mM $CaCl_2$, while levels were near or below the detection limit of the assay for samples treated with thrombin (runs 5 and 6). This contrasts with platelet surface PDI measured by flow cytometry, which was highest in run 6 (thrombin, 20 mM $CaCl_2$). Thus, there appear to be differences between activating conditions with respect to free vs. surface bound PDI. Interestingly, soluble PDI levels were best correlated with released EGF levels ($r=0.566$, $p=0.0001$).

TABLE 3

|  | Run 1 PEF A/ 2.5 mM $CaCl_2$ | Run 2 PEF B/ 2.5 mM $CaCl_2$ | Run 3 PEF A/ 20 mM $CaCl_2$ | Run 4 PEF B/ 20 mM $CaCl_2$ | Run 5 Thrombin/ 2.5 mM $CaCL_2$ | Run 6 Thrombin/ 20 mM $CaCl_2$ | Run 7 Buffered Saline | Run 8 Buffered Saline/ 20 mM $CaCl_2$ |
|---|---|---|---|---|---|---|---|---|
| P-selectin (% +) | 88.7 ± 2.4† | 7.8 ± 2.7* | 83 ± 11.6† | 53.6 ± 32.8*† | 98 ± 1.2† | 98.6 ± 0.4† | 8 ± 3.9* | 18.8 ± 17.2*† |
| P-selectin (MFI) | 52.4 ± 8.5* | 2.2 ± 0.2* | 46.4 ± 24.7* | 74.2 ± 96.3* | 663.8 ± 36*† | 235.6 ± 50.1† | 2.1 ± 0.3* | 4 ± 3.1* |
| TLR9 (% +) | 7.5 ± 2.2* | 7.5 ± 0.9* | 8.1 ± 2* | 25.5 ± 14.7† | 40.3 ± 2.6*† | 22.3 ± 2† | 5.2 ± 1.7* | 7.5 ± 1.3* |
| TLR9 (MFI) | 4.9 ± 0.5 | 5.2 ± 0.8 | 4.9 ± 0.6 | 8.2 ± 2.5† | 10.6 ± 1.7*† | 7 ± 1† | 4.8 ± 0.9* | 5.2 ± 0.7 |
| PDI (% +) | 3.4 ± 1.2* | 1.8 ± 0.4* | 7.2 ± 2.8*† | 3.8 ± 2* | 2.1 ± 0.5* | 14.2 ± 4.1† | 0.8 ± 0.2* | 1.1 ± 0.4* |
| PDI (MFI) | 3.6 ± 0.4* | 4.1 ± 0.6* | 4.1 ± 0.5* | 4.4 ± 0.7* | 3.9 ± 0.9* | 5.5 ± 0.4† | 3.8 ± 0.7* | 3.7 ± 0.5* |

*p < 0.05 vs. thrombin, 20 mM $CaCl_2$;
†p < 0.05 vs. saline.

TABLE 4

| | Run 1 | Run 2 | Run 3 | Run 4 | Run 5 | Run 6 | Run 7 | Run 8 |
|---|---|---|---|---|---|---|---|---|
| | | | | PDI (ng/mL) | | | | |
| | PEF A/ 2.5 mM CaCl$_2$ | PEF B/ 2.5 mM CaCl$_2$ | PEF A/ 20 mM CaCl$_2$ | PEF B/ 20 mM CaCl$_2$ | Thrombin/ 2.5 mM CaCl$_2$ | Thrombin/ 20 mM CaCL$_2$ | Buffered Saline | Buffered Saline/ 20 mM CaCl$_2$ |
| Donor 1 | 9.64 | 3.85 | 3.56 | 3.20 | 3.20 | 3.20 | 4.47 | 3.20 |
| Donor 2 | 5.76 | 4.27 | 4.29 | 3.20 | 3.20 | 3.20 | 5.67 | 3.20 |
| Donor 3 | 9.67 | 6.65 | 7.34 | 5.25 | 3.80 | 5.66 | 7.38 | 6.23 |
| Donor 4 | 5.40 | 4.98 | 3.56 | 3.20 | 3.20 | 3.20 | 3.71 | 3.77 |
| Donor 5 | 7.42 | 4.06 | 5.18 | 3.20 | 3.20 | 3.20 | 3.20 | 3.20 |
| Mean ± SD | 7.6 ± 2*† | 4.8 ± 1.1 | 4.8 ± 1.6 | 3.6 ± 0.9 | 3.3 ± 0.3 | 3.7 ± 1.1 | 4.9 ± 1.7 | 3.9 ± 1.3 |

*$p < 0.05$ vs. thrombin, 20 mM CaCl$_2$;
†$p < 0.05$ vs. saline.
Results below the lower limit of detection are reported using the value of the lower limit (PDI 3.2 ng/mL).

Differential Exposure of Platelet Granules and Growth Factors—Results for this portion of the study are shown in Tables 5 and 6.

shown in Table 6 as a growth factor correlation matrix with corresponding coefficients (r) (top number) and associated probabilities (p values) (bottom number).

TABLE 5

| | Run 1 PEF A/ 2.5 mM CaCl$_2$ | Run 2 PEF B/ 2.5 mM CaCl$_2$ | Run 3 PEF A/ 20 mM CaCl$_2$ | Run 4 PEF B/ 20 mM CaCl$_2$ | Run 5 Thrombin/ 2.5 mM CaCl$_2$ | Run 6 Thrombin/ 20 mM CaCL$_2$ | Run 7 Buffered Saline | Run 8 Buffered Saline/ 20 mM CaCl$_2$ |
|---|---|---|---|---|---|---|---|---|
| PF4 (µg/mL) | 27.1 ± 5.5† | 2.7 ± 1.1* | 15.7 ± 5.3* | 24.5 ± 7.7† | 33.7 ± 12.2† | 32.1 ± 9† | 2.7 ± 0.9* | 18.1 ± 15.2† |
| PDGF (µg/mL) | 7.14 ± 1.53† | 0.70 ± 0.17* | 5.80 ± 1.77*† | 9.56 ± 3.77† | 10.21 ± 3.13† | 10.56 ± 2.38† | 0.82 ± 0.4* | 5.87 ± 3.04*† |
| VEGF (pg/mL) | 363.4 ± 207† | 80.2 ± 26* | 337.7 ± 191.7* | 499 ± 186.5† | 582.3 ± 120.3† | 635.6 ± 241† | 68.5 ± 14.6* | 215.6 ± 188.1* |
| EGF (ng/mL) | 4.81 ± 1.11*† | 0.08 ± 0.00* | 3.35 ± 1.05*† | 0.34 ± 0.19 | 0.33 ± 0.11 | 1.26 ± 0.43† | 0.09 ± 0.02* | 0.20 ± 0.14* |

*$p < 0.05$ vs. thrombin, 20 mM CaCl$_2$;
†$p < 0.05$ vs. saline.
Results below the lower limit of detection are reported using the value of the lower limit (VEGF, 62 pg/mL; EGF 78 pg/mL).

The amount of growth factor released by each treatment condition varied widely but the overall pattern of platelet factor 4 (PF4), platelet-derived growth factor (PDGF), and vascular endothelial growth factor (VEGF) released by treatment was similar.

Figure 8:
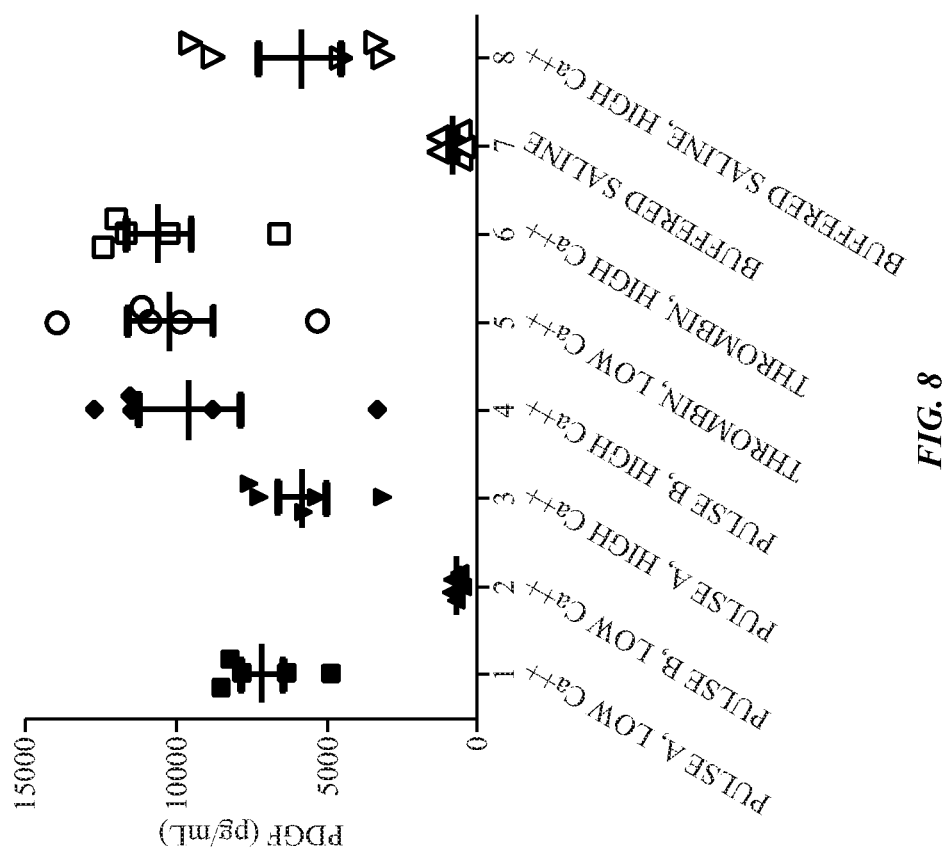
FIG. 8 graphically depicts PDGF levels for a set of study results, in accordance with aspects of the present disclosure.
Figure 7:
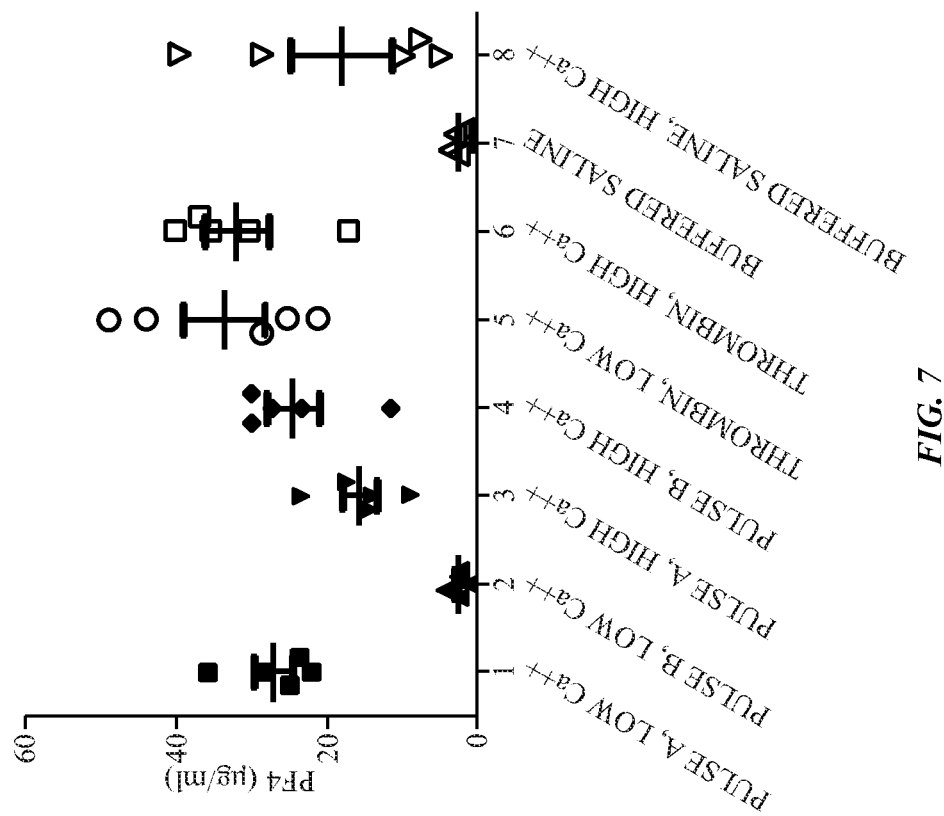
FIG. 7 graphically depicts PF4 levels for a set of study results, in accordance with aspects of the present disclosure.
Figure 10:
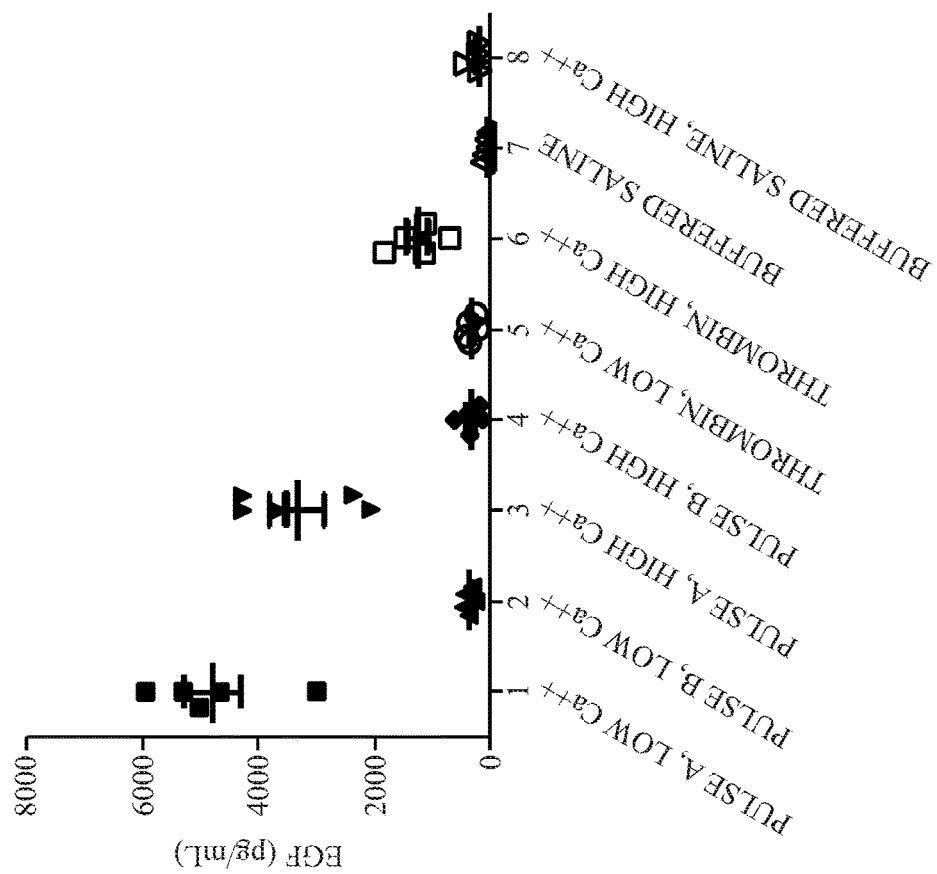
FIG. 10 graphically depicts EGF levels for a set of study results, in accordance with aspects of the present disclosure.
Figure 9:
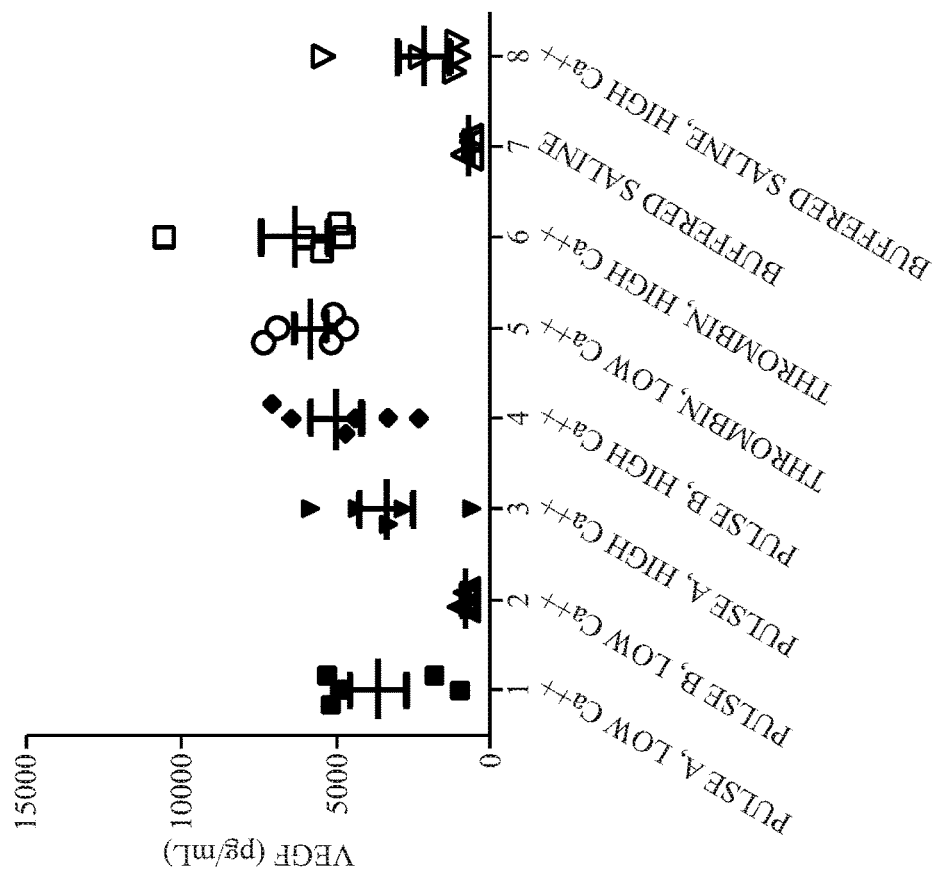
FIG. 9 graphically depicts VEGF levels for a set of study results, in accordance with aspects of the present disclosure.

Specifically, the relative ability of the treatment conditions to increase amounts of PF4, PDGF, and VEGF in supernatants of PRP were, from most to least: run 6 (thrombin, 20 mM CaCl$_2$)≈run 5 (thrombin, 2.5 mM CaCl$_2$)>run 4 (PEF B, 20 mM CaCl$_2$)≈run 1 (PEF A, 2.5 mM CaCl$_2$)>run 2 (PEF A, 20 mM CaCl$_2$)>run 8 (20 mM CaCl$_2$ alone)>run 2 (PEF B, 2.5 mM CaCl$_2$)≈no calcium. These relative relationships are graphically depicted in FIGS. 7, 8, and 9. In each of FIGS. 7, 8, and 9 (as well as in FIG. 10, discussed below), individual results are plotted along with the mean and SEM. Results below the detection limit of the assay are plotted at the lower limit of detection.

In contrast, conditions that yielded the most to least release of EGF were: run 1 (PEF A, 2.5 mM CaCl$_2$)»run 3 (PEF A, 20 mM CaCl$_2$)»run 6 (thrombin, 20 mM CaCl$_2$)>run 5 (thrombin, 2.5 mM CaCl$_2$) run 4 (PEF B, 20 mM CaCl$_2$) run 8 (high calcium alone)>run 2 (PEF B, 2.5 mM CaCl$_2$) run 7 (no calcium). These results are graphically depicted in FIG. 10. Consequently, levels of PF4, PDGF, and VEGF were highly correlated with one another while EGF levels were not correlated with PF4, PDGF, and VEGF, as

TABLE 6

| | PF4 | PDGF | VEGF | EGF |
|---|---|---|---|---|
| PF4 | | r = 0.917 p = 9.2 × 10$^{-17}$ | r = 0.758 p = 1.5 × 10$^{-8}$ | r = 0.264 p = 0.0998 |
| PDGF | r = 0.917 p = 9.2 × 10$^{-17}$ | | r = 0.796 p = 8.34 × 10$^{-10}$ | r = 0.199 p = 0.2179 |
| VEGF | r = 0.758 p = 1.5 × 10$^{-8}$ | r = 0.796 p = 8.34 × 10$^{-10}$ | | r = 0.117 p = 0.4728 |
| EGF | r = 0.264 p = 0.0998 | r = 0.199 p = 0.2179 | r = 0.117 p = 0.4728 | |

With respect to these results and in summary, despite failure of PEF A, 2.5 mM CaCl$_2$ to produce a clot, it did result in significant increase in the percent P-selectin positive platelets, and significant release of PDI, PF4, PDGF, VEGF, and the highest level of released EGF of all rested conditions. In contrast, PEF B, 2.5 mM CaCl$_2$ did not result in a significant increase compared to buffer in P-selectin, TLR9, PDI, or any of the growth factors. In PRP supplemented with 20 mM CaCl$_2$, both PEF A and PEF B increased exposure of the alpha granule marker, P-selectin, to a greater extent than 20 mM CaCl$_2$ alone but to a lesser extent than thrombin, 20 mM CaCl$_2$. The levels of PF4, PDGF, and VEGF, but not EGF correlated with platelet alpha granule release as indicated by platelet surface P-selectin expression (MFI) and with T-granule release as indicated by platelet surface TLR9, while EGF levels, but not PF4, PDGF, or VEGF, correlated with the level of PDI present in the supernatant after activation. Thus, the pattern of EGF release is distinct from that of PF4, PDGF, and VEGF, suggesting that the distribution of EGF within platelets is also distinct from that of these other factors. Potential explanations for the correlation between released soluble PDI with soluble EGF include co-localization in selected platelet granules or localization in distinct granules whose release is triggered by similar stimuli. The enhanced release of EGF by PEF A is potentially useful in clinical situations, given that EGF is important for the epithelialization stage of wound healing.

With the preceding in mind, it is possible to generate an activated platelet product that is customized not only for the growth factors present and their relative proportions, but also in terms of the presence or absence of clotting, and/or, the timing of clot formation. That is, in view of the clotting results described herein, it may be appreciated that the presence of clotting or the time to clot formation onset may be optimized in conjunction with growth factor release. For example, PEF A and PEF B in conjunction with high $Ca^{++}$ (20 mM $CaCl_2$) results in the release of all growth factors tested above control, though in differing relative proportions. In addition, as seen in the above results PEF A in conjunction with low $Ca^{++}$ (2.5 $CaCl_2$) yield an activated product that does not clot but for which all tested growth factors are released. Conversely, PEF B in conjunction with low $Ca^{++}$ yield an activated product that does not clot and for which the tested growth factors are not appreciably released. Therefore appropriate combinations of electrical stimulation and added Ca may be used to control and/or tune the level of growth factors released and the clotting time; when no clotting is desired, appropriate combinations of electrical stimulation and added Ca may be used to release the growth factors at a desired level—high release or low release.

Consolidated and Additional Ca and Electrical Condition Results—In further support of the preceding discussion and results, a further data set showing a range of electrical conditions and calcium ion concentrations along with observed clotting times, clotting strengths, growth factor release, and hemolysis is shown in Table 7. As shown in this additional example, calcium ion concentration and electrical parameters may be jointly varied to obtain a range of responses along differing axes of interest (e.g., clot time, clot strength, growth factor for release (for multiple, independently manipulable growth factors), hemolysis and so forth. In this manner, a multiple attributes of the activated product may be configured by properly selecting one or both of a calcium ion concentration and/or one or more electrical pulse parameters.

As an example from Table 7, samples 2, 3, 4 and 5 have the same type of electrical stimulation, but different levels of added calcium. The clotting time can vary, as a function of added Ca, from 10.2 minutes to 17.4 minutes; for one Ca concentration there is not clotting. This offers a means to control clotting/no clotting and further the actual clotting time for these samples, by simply adjusting the Ca concentration. As one increases the level of added Ca, the level of EGF released increases for these samples—2, 3, 4 and 5—offering a means to tune the growth factors released by adjusting the Ca level, while keeping in this case the same type of electrical stimulation. In a similar manner, the level of hemolysis can be tuned.

| Sample | Electric Pulse Parameters | Added calcium (mM) | Clotting time (min) | Clot strength (mM) | PDGF release vs thrombin (%) | EGF release vs thrombin (%) | % hemolysis vs thrombin (%) |
|---|---|---|---|---|---|---|---|
| 1 | no electric treatment - added thrombin to PRP | 17.04 | 1 | 72.5 | 100.0% | 100.0% | 100.0% |
| 2 | 800 V, ~150-200 ns; 80 bipolar pulses | 5.35 | no clot | no clot | 8.5% | 10.6% | 37.6% |
| 3 | 800 V, ~150-200 ns; 80 bipolar pulses | 8.49 | 17.4 | 70.5 | 105.1% | 49.4% | 26.3% |
| 4 | 800 V, ~150-200 ns; 80 bipolar pulses | 11.61 | 13 | 69.9 | 68.6% | 74.8% | 47.6% |
| 5 | 800 V, ~150-200 ns; 80 bipolar pulses | 17.04 | 10.2 | 72.3 | 88.1% | 436.3% | 57.6% |
| 6 | 500 V, ~200 ns; 1 pulse | 5.35 | no clot | no clot | 1.8% | 8.5% | 22.2% |
| 7 | 500 V, ~200 ns; 1 pulse | 8.49 | 14.2 | 14.2 | 20.9% | 118.7% | 577.0% |
| 8 | 500 V, ~200 ns; 1 pulse | 11.61 | 10.7 | 10.7 | 61.3% | 488.2% | 114.7% |
| 9 | 500 V, ~200 ns; 1 pulse | 17.04 | 11.8 | 77.70 | 90.5% | na | 51.8% |
| 10 | 1.5 kV, ~300 ns; 1 pulse | 5.35 | no clot | no clot | 2.2% | 14.7% | 14.8% |
| 11 | 1.5 kV, ~300 ns; 1 pulse | 8.49 | no clot | no clot | 34.5% | 133.7% | 129.5% |
| 12 | 1.5 kV, ~300 ns; 1 pulse | 11.61 | 10.5 | 79.3 | 100.8% | 138.6% | 66.6% |
| 13 | 1.5 kV, ~300 ns; 1 pulse | 17.04 | 11.2 | 74.6 | 88.3% | 560.1% | 1702.8% |
| 14 | 2 kV, ~400 ns; 1 pulse | 8.49 | no clot | no clot | 4.9% | 9.9% | 22.2% |
| 15 | 2 kV, ~400 ns; 1 pulse | 11.61 | 13.6 | 74.9 | 44.1% | 167.0% | 55.5% |
| 16 | 1.7 kV, 5 μs; 1 pulse | 5.35 | no clot | no clot | 58.2% | 423.8% | 43.8% |
| 17 | 1.7 kV, 5 μs; 1 pulse | 8.49 | 14.2 | 65.5 | 96.2% | 642.2% | 65.1% |
| 18 | 1.7 kV, 5 μs; 1 pulse | 11.61 | 7.9 | 70.6 | 85.3% | 690.5% | 208.8% |
| 19 | 1.7 kV, 5 μs; 1 pulse | 17.04 | 5.9 | 65.5 | 67.4% | 695.3% | 236.0% |

-continued

| Sample | Electric Pulse Parameters | Added calcium (mM) | Clotting time (min) | Clot strength (mM) | PDGF release vs thrombin (%) | EGF release vs thrombin (%) | % hemolysis vs thrombin (%) |
|---|---|---|---|---|---|---|---|
| 20 | 3.4 kV, 5 µs; 1 pulse | 5.35 | no clot | no clot | 54.3% | 626.5% | 576.0% |
| 21 | 3.4 kV, 5 µs; 1 pulse | 8.49 | 12.6 | 40.8 | 50.6% | 580.4% | 222.4% |
| 22 | 3.4 kV, 5 µs; 1 pulse | 11.61 | 6.6 | 31.1 | 60.3% | 652.2% | 154.4% |
| 23 | 3.4 kV, 5 µs; 1 pulse | 17.04 | 5.9 | 30.6 | 50.1% | 510.9% | 161.2% |

Thus, as shown in Table 7, a variety of different electrical properties and pulse parameters may be varied in conjunction with calcium ion concentration to achieve a variety of different clotting times and strengths, while still controlling for individual levels of growth factor release and hemolysis.

Technical effects of the invention include generation of an activated platelet product in which one or more of the presence or absence of clots, the timing of clot formation (if present), and/or the mechanical strength of clots (if present) is controlled by the presence or concentration of calcium ions during the activation process. The calcium ion concentration is controlled or specified in the presence of pulsed electric fields or a chemical activator (e.g., thrombin) as part of the activation process.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

If any claims appended to the end of this specification contain one or more elements designated as "means for [perform]ing [a function] . . . " or "step for [perform]ing [a function] . . . , then it is intended that such elements are to be interpreted under 35 U.S.C. 112(f). However, for any claims containing elements designated in any other manner, then it is intended that such elements are not to be interpreted under 35 U.S.C. 112(f).

The invention claimed is:

1. A method for generating an activated product comprising:
   preparing a platelet-rich plasma (PRP) sample for activation by adding a reagent comprising calcium ions to the PRP sample, wherein the prepared PRP sample comprises a first calcium ion concentration, wherein the first calcium ion concentration is selected based upon target levels of one or more growth factors and clotting characteristics in the activated product generated using the PRP sample, the clotting characteristics comprising a time of formation of a clot or mechanical strength of the clot, or any combination thereof;
   positioning the prepared PRP sample between electrodes of an electromagnetic stimulation apparatus;
   specifying a set of electrical pulse parameters based upon the first calcium ion concentration and the clotting characteristics; and
   exposing the prepared PRP sample to one or more electrical pulses generated in accordance with values of the set of electrical pulse parameters, wherein the PRP sample, when exposed to the one or more electrical pulses, yields the activated product comprising target levels of the one or more growth factors and the clotting characteristics.

2. The method of claim 1, wherein the same set of electrical pulse parameters but different concentrations of calcium ions yield differences in the clotting characteristics in the activated product.

3. The method of claim 1, wherein the PRP sample comprises a platelet gel, a platelet suspension, or a whole blood sample.

4. The method of claim 1, wherein relative levels of the growth factors in the activated product are determined by one or both of the set of electrical pulse parameters and the first calcium ion concentration.

5. The method of claim 1, wherein adding the reagent comprises adding $CaCl_2$ to an anticoagulant-treated PRP sample, and wherein the first calcium ion concentration is in a range of about 2.5 mM to about 20 mM.

6. The method of claim 1, wherein the first calcium ion concentration is selected from 2.5 mM, 5.0 mM, 7.5 mM, 10 mM, 15 mM, 20 mM, or 25 mM $CaCl_2$ being added to the anticoagulant-treated PRP sample.

7. The method of claim 1, wherein the first calcium ion concentration is selected based on the time of formation of the clotting.

8. The method of claim 1, wherein the first calcium ion concentration is selected based on a clot mechanical strength.

9. The method of claim 1, wherein the growth factors comprise epidermal growth factor (EGF), platelet-derived growth factor (PDGF), vascular endothelial growth factor (VEGF), or platelet factor 4 (PF4), or any combination thereof.

10. A method for generating an activated product comprising:
    preparing an anticoagulant-treated platelet-rich plasma (PRP) sample for activation;
    adding calcium ions to the PRP sample to achieve a calcium ion concentration selected from a range of possible concentrations, wherein the concentration is selected based upon target levels of one or more growth factors to be present in an activated product composition generated using the PRP sample and wherein one or more clotting characteristics are also determined by the calcium ion concentration; and exposing
    the PRP sample to electrical activation stimulus, wherein the PRP sample, when exposed to the electrical activation stimulus, yields an activated product composition comprising the one or more growth factors at the target levels and the one or more clotting characteristics, wherein varying the calcium ion concentration without varying the electrical activation stimulus changes one or both of the absolute or relative levels of the one or more growth factors.

11. The method of claim 10, wherein adding calcium ions to the PRP sample comprises adding $CaCl_2$ to the PRP sample in a concentration in the range of about 2.5 mM to about 20 mM.

12. The method of claim 10, wherein the concentration of calcium ions is selected from a plurality of possible concentrations corresponding to 2.5 mM, 5.0 mM, 7.5 mM, 10 mM, 15 mM, 20 mM, or 25 mM $CaCl_2$ being added to the PRP sample.

13. The method of claim 10, wherein a first calcium concentration that is less than a second calcium ion concentration results in an initial clot formation that is quicker than that observed at the second calcium ion concentration.

14. The method of claim 10, wherein a first calcium concentration that is less than a second calcium ion concentration results in a clot mechanical strength that is less than that observed at the second calcium ion concentration.

15. A method for controlling clot mechanical strength in a platelet gel, comprising:
   determining a prospective mechanical strength of one or more clots to be generated in the platelet gel, wherein the prospective mechanical strength is greater than what would be observed by generating the platelet gel using thrombin alone; determining target levels of one or more growth factors; based
   on the prospective mechanical strength and target levels of one or more growth factors, selecting a calcium ion concentration based upon the target levels of one or more growth factors and corresponding to the prospective mechanical strength from among a plurality of calcium ion concentrations; and generating;
   the platelet gel by activating a platelet-rich plasma (PRP) sample comprising calcium ions at the selected calcium ion concentration, wherein the PRP sample is activated using electrical stimulus, and wherein the platelet gel comprises clots that, once formed, have the prospective mechanical strength and comprise the target levels of the one or more growth factors.

16. The method of claim 15, wherein, for the plurality of calcium ion concentrations, higher calcium ion concentrations correspond to greater mechanical strength of the clots.

17. The method of claim 15, wherein the plurality of calcium ion concentrations is within a range corresponding to what is generated by addition of about 2.5 mM to about 20 mM $CaCl_2$ to the PRP sample.

18. The method of claim 17, wherein the calcium ion concentration is selected from the plurality of possible concentrations corresponding to 2.5 mM, 5.0 mM, 7.5 mM, 10 mM, 15 mM, 20 mM, or 25 mM $CaCl_2$ being added to the PRP sample.

* * * * *